United States Patent [19]

Wang

[11] Patent Number: 5,071,996

[45] Date of Patent: Dec. 10, 1991

[54] BENZHETEROCYCLIC COMPOUNDS

[75] Inventor: Pen-Chung Wang, Houston, Tex.

[73] Assignee: Shell Oil Company, Houston, Tex.

[21] Appl. No.: 607,785

[22] Filed: Oct. 26, 1990

Related U.S. Application Data

[63] Continuation of Ser. No. 351,509, May 15, 1989, abandoned.

[51] Int. Cl.$^5$ .................. C07D 235/04; C07D 235/02
[52] U.S. Cl. .................................... 548/328; 548/156;
548/219; 548/326; 546/256; 546/271; 544/80
[58] Field of Search ............... 548/156, 219, 326, 328;
546/256, 271; 544/80

[56] References Cited

U.S. PATENT DOCUMENTS 1,999,181  4/1935  Conover et al. .................. 260/64

OTHER PUBLICATIONS

Cava et al., *J. Am. Chem. Soc.*, 77, p. 6022 (1955).
Cava et al., *J. Am. Chem. Soc.*, 79, p. 1706 (1957).
Sikes et al., "ACS Meeting Minutes", Apr. 1989, Dallas, p. 614.

*Primary Examiner*—Johann Richter

[57] ABSTRACT

Novel hydroxy-benzoheterocyclic-substituted 3-oxopentane derivatives are produced by reaction of a hydroxy-containing ortho-phenylene amine compound and the source of a five-carbon keto-containing moiety selected from 4-oxoheptanedioic acid compounds or 1,6-dioxa[4.4]spirodilactones. The derivatives produced from hydroxy-phenylenediamines are further reacted to produce compounds of higher cyclic functionality.

7 Claims, No Drawings

BENZHETEROCYCLIC COMPOUNDS

This is a continuation of application Ser. No. 351,509, filed May 15, 1989, now abandoned.

FIELD OF THE INVENTION

This invention relates to certain novel hydroxy-containing benzoheterocyclic compounds and to processes for the production thereof. More particularly, the invention relates to the products of the reaction of a hydroxy-containing ortho-phenylene amine compound with a 4-oxoheptanedioic acid compound or a 1,6-diaza[4.4]spirodilactone and cyclized derivatives of certain such products.

BACKGROUND OF THE INVENTION

The class of aromatic bisphenols is well known in the art. A commercial example of such a compound is 2,2-di(4-hydroxyphenyl)propane, also known as bisphenol A or BPA. The bisphenols are particularly useful as monomeric precursors of polymers of a variety of types. Reaction of a bisphenol with a haloepoxyalkane, e.g., epichlorohydrin, results in the production of the corresponding glycicyloxy derivative which reacts with a number of conventional curing agents to produce thermoset resins having good properties of strength and rigidity. The allyloxy or proparglyloxy derivatives of the bisphenols are also curable to produce thermoset resins. Alternatively, reaction of an alkali metal salt of the bisphenol with a di(halophenyl) sulfone or a di(-halophenyl) ketone results in the production of thermoplastic polymers of the phenoxy type.

Bisphenols containing additional cyclic structures are particularly desirable when polymers to be employed in high temperature applications are desired. Such bisphenols are precursors of polymers, both thermoplastic and thermoset, which frequently have relatively high melting points or glass transition temperatures. These polymers find particular utility when dimensional stability is required for a polymer likely to be exposed to elevated temperatures. It would be of advantage to provide novel bisphenols having a plurality of types of cyclic structure within the bisphenol molecule.

SUMMARY OF THE INVENTION

The present invention relates to novel heterocyclic bisphenols as well as to the process for the production thereof. More particularly, the invention relates to the reaction of, and reaction productions derived therefrom, a hydroxy-containing ortho-phenylene amine compound and a source of a five-carbon keto-containing moiety, which source is selected from a 4-oxoheptandioic acid compound or a 1,6-dioxa[4.4]spirodilactone.

DESCRIPTION OF THE INVENTION

The novel compounds of the invention are characterized by the presence of two hydroxy-substituted benzoheterocyclic moieties. In one modification of the compounds of the invention, the hydroxy-substituted benzoheterocyclic moieties are connected by a five-carbon connecting group having a carbonyl group, i.e., a keto group, in the center or 3 position. The source of this five-carbon keto-containing group, i.e., a keto-$C_3$ group, is a 4-oxoheptanedioic acid compound or a 1,6-dioxa [4.4]spirodilactone. The products in this modification of the compounds of the invention are 1,5-di(benzoheterocyclic)-3-oxopentane compounds. In a second modification of the compounds of the invention, certain of the heterocyclic 3-oxopentane products undergo internal dehydration to produce products of greater cyclic functionality.

In one embodiment of the process of the invention, the keto-$C_5$ source is a ketodicarboxylic acid compound having two carbon atoms between the keto group and each carboxy function. Expressed in other terms, the keto-$C_5$ source is a 4-oxoheptanedioic acid compound. Although a variety of such 4-oxoheptanedioic acid compounds having a variety of substituents in addition to the keto group and the carboxy functions, the preferred 4-oxoheptanedioic acid compounds have up to 30 carbon atoms and are represented by the formula

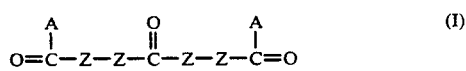

wherein A independently is hydroxy, alkoxy, preferably lower alkoxy of up to 4 carbon atoms, or halo, preferably the middle halogens chloro or bromo. The term Z independently is $>C(Z')_2$ in which Z' independently is hydrogen, lower alkyl, preferably methyl, halo, preferably the lower halogens fluoro or chloro, or aryl, preferably phenyl, or Z is such that two adjacent Z groups taken together form a ring system Z'' of from 5 to 7 ring atoms up to two of which are heteroatoms selected from nitrogen, oxygen or sulfur with the remainder of the ring atoms being carbon atoms, there being up to 15 carbon atoms in each Z'', two of which form a bridge between the carbon atoms connected by the adjacent Z groups. When adjacent Z groups are Z'', the ring system is aromatic, cycloaliphatic or heterocyclic and is otherwise hydrocarbyl containing only atoms of carbon and hydrogen besides any heteroatoms or is substituted hydrocarbyl containing additional atoms in the form of inert, carbon atom substituents, e.g., halogen atoms, preferably middle halogen atoms.

In a first aspect of the use of the ketodiacid compounds as a keto-$C_5$ source, each Z is not part of a fused ring system and is therefore acyclic, i.e., each Z is $>C(Z')_2$, and the ketodicarboxylic acid is an acyclic 4-oxoheptanedioic acid compound. Such 4-oxoheptanedioic acid compounds are represented by the formula

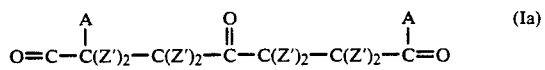

wherein Z' and A have the previously stated meanings. These acid compounds are illustrated by 4-oxoheptanedioic acid, dimethyl 4-oxoheptanedioate, 3,5-diphenyl-4-oxoheptanedioic acid, 2,3,5,6-tetramethyl-4-oxoheptanedioyl chloride, di-n-propyl 2,6-di-n-butyl-4-oxoheptanedioate, 3-methyl-4-oxoheptanedioic acid and 6-carbomethoxyhexanoic acid. The preferred compounds of the above formula Ia are those wherein each Z' is preferably hydrogen or methyl, expecially hydrogen, and each A is hydroxy or alkoxy, particularly hydroxy.

The ketodicarboxylic acids of formula Ia are known compounds or are produced by known methods but certain of the esters of formula Ia, i.e., the compounds wherein A is alkoxy, are conveniently produced by the reaction of formaldehyde with an unsaturated carboxylic acid ester such as methyl acrylate, ethyl methacrylate, methyl crotonate and propyl 2,3-dimethyl-2-butenoate. This reaction, conducted in the presence of a thiazolium compound and a tertiary amine as a catalyst system, produces the 4-oxoheptanedioate derivatives in good yield. The process is described in more detail and claimed in U.S. Pat. No. 4,800,231. The conversion of the esters thereby obtained to the corresponding acids or acid halides is by conventional methods.

In a second aspect of the use of a ketodicarboxylic acid compound as a keto-$C_5$ source, the ketodiacid incorporates fused cyclic substituents between the keto group and the carboxy functions, i.e., the two adjacent Z moieties form a cyclic ring system $Z''$. Such diacid compounds are represented by the formula

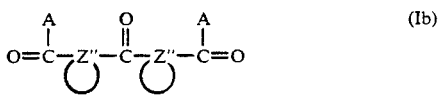

(Ib)

wherein $Z''$ has t stated meaning. Illustrative of these cyclic ketodiacid compounds are di(2-carboxyphenyl) ketone, di(2-carboxycyclohexyl) ketone, di(2-chlorocarbonylphenyl) ketone, di(2-carboxypyridyl) ketone, 2-carboxyphenyl N-methyl-3-carboxy-2-pyrrl ketone, di(3-carbomethoxy-2-morpholyl) ketone and di(2-carbethoxyphenyl) ketone. The preferred compounds of formula Ib are those wherein each $Z''$ is a ring system of from 5 to 6 ring atoms including up to one nitrogen atom, preferably a ring system of 6 carbon atoms. The cyclic 4-oxoheptanedioic acid compounds of formula Ib are known compounds or are produced by known methods, for example, the process of Conover et al, U.S. Pat. No. 1,999,181, or the method of Cava et al, J. Am. Chem. Soc, 20, 6022 (1955).

In yet another aspect of the use of the 4-oxoheptanedioic acid compound as the keto-$C_5$ source, the ketodiacid incorporates one fused ring substituent with the remainder of the Z groups being acyclic, i.e., the compounds represented by the formula

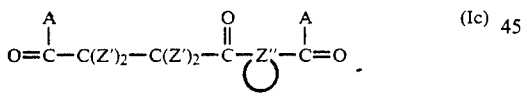

(Ic)

wherein A, $Z'$ and $Z''$ have the previously stated meaning. Such ketodiacid compounds of one cyclic fused ring substituent are exemplified by 3-(2-carboxybenzoyl)propionic acid, 3-(3-carbomethoxy-2-pyridyloyl)-2-ethylpropionic acid, ethyl 3-(2-carbethoxybenzoyl)propionate and 3-(2-carboxy-4-methylbenzoyl)propionate. The ketoacid compounds of formula Ic are known compounds or are produced by known methods. For example, 2-carbomethoxybenzaldehyde reacts with methyl acrylate according to the general teachings of copending U.S. patent application Ser. No. 1"⋅999, filed Mar. 23, 1988.

In a second embodiment of the hydroxy-containing ortho-phenylene amine compound reacting with a keto-$C_5$ source, the keto-$C_5$ source is a 1,6-dioxa4.4]-spirodilactone in which the spiro ring system is substituted with a variety of monovalent or fused ring substituents. One class of such [4.4]spirodilactones is represented by the formula

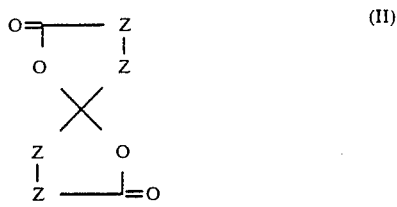

(II)

wherein Z has the previously stated meaning.

In one aspect of the use of these spirodilactones as the keto-$C_5$ source, each Z is acyclic, i.e., each Z is $>C(Z')_2$, and the spirodilactone compounds are represented by the formula

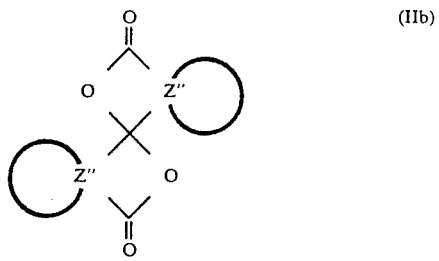

(IIa)

wherein $Z'$ has the previously stated meaning. Illustrative of such spirodilactones are 1,6-dioxaspiro[4.4]nonane-2,7-dione, 3,8-dimethyl-1,6-dioxaspiro[4.4]nonane-2,7-dione, 3,4,8,9-tetramethyl-1,6-dioxaspiro[4.4]nonane-2,7-dione, 4,9-diphenyl-1,6-dioxaspiro[4.4]nonane-2,7-dione, 3,3,4,4,8,8,9,9-octamethyl-1,6-dioxaspiro[4.4]nonane-2,7-dione and 3,4,8,9-tetrafluoro-1,6-dioxaspiro[4.4]nonane-2,7-dione. The preferred spirodilactones of the above formula IIa are those wherein at least one $Z'$ of each $Z'$-substituted carbon atom is hydrogen. The compounds of formula IIa are known compounds or are produced by known methods, e.g., the process of Pariza et al, Synthetic Communications, Vol. 13(3), pp. 243-254 (1983).

In a second aspect of the use of spirodilactones as the keto-$C_5$ source, a cyclic, fused ring substituent is present on each of the two spiro rings, i.e., adjacent Z groups are $Z''$. Such spirodilactones are represented by the formula (IIb)

wherein $Z''$ has the previously stated meaning. The spirodilactones of this class are illustrated by 3,4,8,9-dibenzo-1,6-dioxaspiro[4.4]nonane-2,7-dione, 3,4,8,9-di(cyclopentano)-1,6-dioxaspiro[4.4]nonane-2,7-dione, 3,4,8,9-di-4-methylbenzo)-1,6-dioxaspiro[4.4]nonane-2,7-dione and 3,4,8,9-di(pyrido)-1,6-dioxaspiro[4.4]nonane-2,7-dione. These compounds are known compounds or are produced by known methods, for example, the process of the above Cava et al article or by the process of U.S. Pat. No. 1,999,181.

In a third aspect of the use of spirodilactones as the keto-$C_5$ source, a cyclic substituent is fused to one spiro ring and the other spiro ring is free of fused cyclic substituents, e.g., spirodilactones of the formula

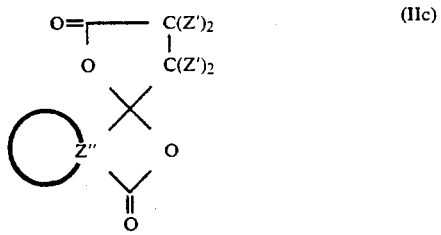
(IIc)

wherein Z' and Z" have the previously stated meanings. Such spirodilactones are illustrated by 3,4-benzo-8-methyl-1,6-dioxaspiro[4.4]nonane-2,7-dione, 3,4-pyrido-1,6-dioxaspiro[4.4]nonane-2,7-dione, 3,4-benzo-8,9-diphenyl-1,6-dioxaspiro[4.4]nonane-2,7-dione and 3,3,4,4-tetramethyl-8,9-morpholo-1,6-dioxaspiro[4.4]nonane-2,7-dione. The spriodilactones of formula IIc are known compounds or are produced by known methods, for example, by the dehydration of the corresponding ketodicarboxylic acid. By way of specific illustration, 3,4-benzo-1,6-dioxaspiro4.4]nonane-2,7-dione is produced by dehydration of 3-(Z-carboxybenzoyl)propionic acid upon application of heat.

In general, the preferred spirodilactones to be used as a keto-$C_5$ source are hydrocarbon except for the oxygens of the lactone moieties and particularly preferred are those spirodilactones which are free from cyclic fused ring substituents (formula IIa) or which have a fused ring substituent on each of the spiro rings (formula IIb). An especially preferred spirodilactone of the former class is 1,6-dioxaspiro[4.4]nonane-2,7-dione whereas an especially preferred member of the latter class is 3,4,8,9-dibenzo-1,6-dioxaspiro[4.4]nonane-2,7-dione.

The keto-$C_5$ source is reacted in the process of the invention, whether a 4-oxoheptanedioic acid compound or a spirodilactone, with a hydroxy-containing ortho-phenylene amine compound. These amine compounds are organic compound having at least one aromatic ring containing an amino substituent, i.e., a-$NH_2$ group, and having as a substituent on a ring carbon atom adjacent to the carbon atom on which the amino group is located a second substituent which is amino, alkylamino, hydroxy or thiol. A third substituent, a hydroxy substituent, is located on a ring carbon atom which is not adjacent to either of the carbon atoms on which the amino substituent or the second substituent is located. One class of such hydroxy-containing o-phenylene amine compounds is represented by the formula

(III)

wherein Y is amino, alkylamino, hydroxy or thiol and R is aromatic of up to 20 carbon atoms and from 1 to 2 aromatic rings, inclusive, having, when two rings are present, rings which are fused or are connected by a direct valence bond, alkylene of up to 8 carbon atoms inclusive, oxy, thio, sulfonyl or carbonyl. When R has two rings, it is generally preferred that the third substituent, i.e., the hydroxy group, is located on one aromatic ring and that the amino group and the second substituent are located on the other ring, although such is not required. R is otherwise hydrocarbyl containing only atoms of carbon and hydrogen in addition to any other atoms present in the divalent connecting groups, or R is substituted hydrocarbyl containing other atoms present as inert carbon atom substituents, e.g., atoms such as halogen, preferably middle halogen.

Illustrative of the hydroxy-containing o-phenylene amine compounds are 3,4-diaminophenol, 4,5-diamino-3-methyl-phenol, 5-hydroxy-2,3-diaminonaphthalene, 3,4-diamino-4'-hydroxybiphenyl, 4-(4-hydroxyphenyloxy)-1,2-diaminobenzene, 3-(4-hydroxybenzoyl)-1,2-diaminobenzene, 4-aminoresorcinol, 4-(3-hydroxyphenylthio)-2-aminophenol, 3-hydroxyphenyl-2-aminothiophenol, 2-amino-1,5-dihydroxynaphthalene, 3-amino-4-ethylaminophenol, 3-(4-hydroxyphenylsulfonyl)-2-aminothiophenol and 3-amino-2-propylamino-3'-hydroxybiphenyl. In general, the hydroxy-containing o-phenylenediamines are preferred over the corresponding hydroxy-containing alkylaminoamines, aminophenols or aminothiophenols. The compound 3,4-diaminophenol is particularly satisfactory.

The reaction of the keto-$C_5$ source and the hydroxy-containing o-phenylene amine compound is conducted in the liquid phase under reaction conditions in the presence of an inert reaction diluent. Suitable reaction diluents are liquid under reaction conditions and are polar diluents capable of dissolving at least a portion of each reactant at reaction temperature. Such diluents include ketones such as methyl isobutyl ketone and di-n-propyl ketone, esters such as ethyl 2-ethylhexanoate, ethers including acyclic ethers such as diethylene glycol diethyl ether and tetraethylene glycol dimethyl ether as well as cyclic ethers such as tetrahydrofuran and dioxane, N-alkylamides such as N,N-dimethylformamide, N,N-dimethylacetamide and N-methyl-2-pyrrolidone, phenols such as phenol and m-cresol, and sulfur-containing diluents such as dimethyl sulfoxide and sulfolane. The preferred reaction diluent is m-cresol.

The keto-$C_5$ source and the hydroxy-containing o-phenylene amine compound combine in a molar ratio of 1:2 to produce a heterocyclic bisphenol according to the process of the invention. It is satisfactory in practice to provide the keto-$C_5$ source and the hydroxy-containing o-phenylene diamine compound in a molar ratio of from about 2:1 to about 1:8 and even higher or lower ratios can be used. Molar ratios of from about 1:1 to about 1:4 are preferred. Suitable reaction temperatures are from about 125° C. to about 250° C, preferably from about 150° C. to about 225° C., depending in part on the particular reaction diluent to be employed. The reaction pressure will be sufficient to maintain the reaction mixture in the liquid phase at reaction temperature. Typical reaction pressures will be up to about 20 atmospheres but more often from about 0.8 atmospheres to about 10 atmospheres. During reaction, the contact of the reactants is maintained by conventional methods such as shaking, stirring or refluxing and subsequent to reaction the heterocyclic bisphenol product is recovered by well-known methods such as extraction, precipitation or solvent removal.

Reaction of the keto-$C_5$ source and the hydroxy-containing o-phenylene amine compound results in the production of a hydroxy-substituted benzoheterocyclic compound which incorporates one carbon atom of the keto-$C_5$ source in each of the two heterocyclic ring systems, which ring systems are connected by the residual five-carbon bridge of the keto-$C_5$ source wherein an oxo group or a keto group is located in the center or the 3-position of the five-carbon bridge. The benzoheterocyclic product resulting from the reaction of the keto-$C_5$ source and the hydroxy-containing o-phenylene compound is a benzimidazoyl derivative, a benzoxazoyl derivative or a benzothiazoyl derivative if the hydroxy-containing o-phenylene amine compound is a diamine, an aminophenol or an aminothiophenol, respectively. In terms of the keto-$C_5$ source of either formula I or formula II and the hydroxy-containing o-phenylene amine compounds of formula III, the heterocyclic products are represented by the formula

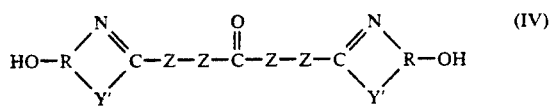

wherein R and Z have the previously stated meanings and Y' is the moiety derived by loss of a hydrogen from Y, that is, Y' is imino, alkylimino, oxa or thio. In terms of the preferred reactants of formulas I or II and III, the preferred products of formula IV are those wherein Y' is imino and Z is >$CH_2$ or adjacent Z groups are benzo.

Illustrative of such products are 1,5-di(5-hydroxy-2-benzimidazoyl)-3-oxopentane illustratively produced from 3,4-diaminophenol and either 4-oxoheptanedioic acid or 1,6-dioxaspiro[4.4]nonane-2,7-dione, 1,5-di(6-hydroxy-N-methyl-Z-benzimidazoyl)-1,2,4,5-dibenzo-3-oxopentane illustratively produced from 5-hydroxy-2-methylamino-aniline and either di(2-carboxyphenyl) ketone or 3,4,8,9-dibenzo-1,6-dioxaspiro[4.4]nonane-2,7-dione, 1,5-di(5-hydroxy-6-methyl-2-benzothiazoyl)-1,5-dimethyl-3-oxopentane illustratively produced from 2-amino-4-hydroxy-5-methylthiphenol and either 2,6-dimethyl-4-oxoheptanedioic acid or 3,8-dimethyl-1,6-dioxaspiro[4.4]-nonane-2,7-dione, and 1,5-di(5-hydroxy-2-benzoxazoyl)-3-oxopentane produced from 4-aminoresorcinol and either dimethyl 4-oxoheptanedioate or 1,6-dioxaspiro[4.4]nonane-2,7-dione. Other products will be apparent from consideration of the above formulas for the reactants and the heterocyclic bisphenol product.

The heterocyclic bisphenolic products (formula IV) of the invention are aromatic dihydroxy compounds and are precursors of a variety of polymeric products obtained by procedures which are conventional for bisphenol compounds. For example, the bisphenols of formula IV are reacted with di(chlorophenyl) sulfone to produce a thermoplastic polymer having good properties and dimensional stability at elevated temperatures. The products are alternatively employed as precursors of thermoset resins as by conversion of the bisphenol to the alkali metal salt by treatment with alkali metal base and reaction of the salt thereby obtained with allyl bromide to produce the bis(allyloxy) derivative which is cured by reaction with conventional curing agents, e.g., a bis(maleimide).

A somewhat special case exists when the hydroxy-substituted benzoheterocyclic product of formula IV is produced from a hydroxy-substituted o-phenylenediamine and Y' is therefore imino. Such products are represented by the formula

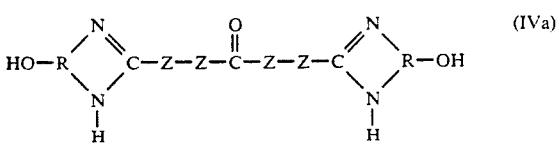

By virtue of the unique relationship of the active hydrogen of each imino group and the carbonyl group in the 3-position of the five-carbon connecting bridge, dehydration to produce a product of greater cyclic functionality is possible whereas such dehydration cannot occur when Y' is other than imino because of the absence of active hydrogens. Such dehydrated products of higher cyclic functionality are represented by the formula

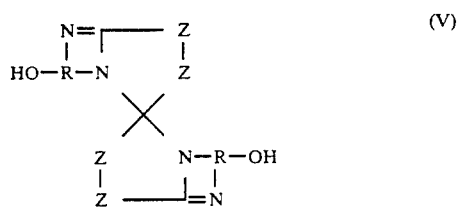

Such products of formula V are 3,4,8,9-di(hydroxybenzimidazo)-1,6-diazaspiro[4.4]nonanes wherein R and Z have the previously stated meanings. By way of specific illustration, the initial product of 3,4-diaminophenol and 4-oxoheptanedioic acid, 1,5-di(5-hydroxy-2-benzimidazoyl)-3-oxopentane, undergoes dehydration (cyclization) upon application of heat to produce 3,4,8,9-di(5-hydroxybenzimidazo)-1,6-diazaspiro[4.4]nonane of the formula

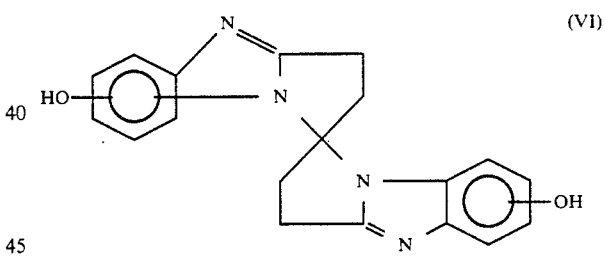

An additional illustrative product of this type is 3,4,8,9-di[5-(4-hydroxyphenyl)benzimidazo]-1,6-diazaspiro[4.4]nonane illustratively produced by heating the initial reaction product from the reaction of 3,4-diamino-4'-hydroxybiphenyl and 1,6-dioxaspiro[4.4]nonane-2,7-dione. Other products will be apparent from consideration of the formulas for the reactants (formula IVa) and the product of higher cyclic functionality (formula V).

Conversion to the benzimidazo derivatives of formula V is accomplished by heating the benzimidazoyl derivatives of IVa to a temperature above about 250° C. in a reaction diluent which is the same diluent as that in which the benzimidazoyl derivative was produced or which is a different polar reaction diluent in which the formula IVa compound is at least partially soluble. It is particularly convenient to employ a diluent or mixture of diluents including a diluent with which water forms an azeotrope so that the water formed by the process of dehydrating the benzimidazoyl derivative to the benzimidazo derivative is easily removed as an azeotrope. Subsequent to the heating/dehydration process the hydroxy-containing hydrocybenzimidazo derivatives (formula V) are recovered by conventional methods The hydroxy-containing benzimidazo derivatives of the invention are bisphenols and as such are useful precursors of polymeric materials of both the thermoplastic and thermoset types. Conversion of these bisphenols to polymeric derivatives is by conventional methods such as are described above. The resulting polymers, in part because of the polycyclic structure, are characterized by quite high melting points or glass transition temperatures and are particularly useful in high temperature applications.

The invention is further illustrated by the following Illustrative Embodiments which should not be construed as limiting.

ILLUSTRATIVE EMBODIMENT I

When a mixture of 3,4-diaminophenol and 4-oxoheptanedioic acid is heated in m-cresol, and the resulting mixture is cooled and poured into methylene chloride, a product will precipitate whose nuclear magnetic resonance spectra will be consistent with a product containing 1,5-di(5-hydroxy-2-benzimidazoyl)-3-oxopentane.

ILLUSTRATIVE EMBODIMENT II

When the product of Illustrative Embodiment I is heated in toluene until water removal is complete, pouring the mixture which results into methylene chloride will afford a product of high melting point whose nuclear magnetic resonance spectra will be consistent with a product containing 3,4,8,9-di(5-hydroxy-2-benzimidazo)1,6-diazaspiro[4.4]nonane.

What is claimed is:

1. A 1,5-di(hydroxybenzoheterocyclic)-3-oxopentane compound of the formula

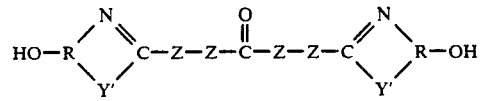

wherein R is an aromatic group having one aromatic ring, Y' is amino, alkylimino, oxa or thio, and Z independently is $>C(Z')_2$ in which Z' independently is hydrogen, lower alkyl, halo or aryl, with the proviso that the ring carbon on which the hydroxy group of each benzoheterocyclic substituent is located is not adjacent to the carbon atom on which the N moiety or the Y' moiety is located and that the N moiety and the Y' moiety of each benzoheterocyclic substituent are located on adjacent ring carbon atoms.

2. The compound of claim 1 wherein Z' is hydrogen or methyl.

3. The compound of claim 2 wherein Y' is oxa.

4. The compound of claim 2 wherein Y' is thio.

5. The compound of claim 2 wherein Y' is alkylimino.

6. The compound of claim 2 wherein Y' is imino.

7. The compound of claim 6 of the structure 1,5-di(5-hydroxy-2-benzimidazoyl)-3-oxopentane.

* * * * *